(12) United States Patent
Azhari et al.

(10) Patent No.: US 9,107,798 B2
(45) Date of Patent: Aug. 18, 2015

(54) METHOD AND SYSTEM FOR LIPOLYSIS AND BODY CONTOURING

(75) Inventors: Haim Azhari, Doar-Na Misgav (IL); Jacob Benarie, Haifa (IL); Yossi Gross, Moshav Mazor (IL)

(73) Assignee: SLENDER MEDICAL LTD., Herzliya (IL)

( * ) Notice: Subject to any disclaimer, the term of this patent is extended or adjusted under 35 U.S.C. 154(b) by 587 days.

(21) Appl. No.: 11/653,115

(22) Filed: Jan. 12, 2007

(65) Prior Publication Data
US 2007/0239077 A1    Oct. 11, 2007

Related U.S. Application Data

(63) Continuation-in-part of application No. 11/651,198, filed on Jan. 8, 2007, now Pat. No. 7,828,734.

(60) Provisional application No. 60/780,772, filed on Mar. 9, 2006, provisional application No. 60/809,577, filed on May 30, 2006, provisional application No. 60/860,635, filed on Nov. 22, 2006.

(51) Int. Cl.
*A61H 1/00*    (2006.01)
*A61B 8/00*    (2006.01)
*A61H 23/02*    (2006.01)
(Continued)

(52) U.S. Cl.
CPC .............. *A61H 23/0245* (2013.01); *A61B 8/08* (2013.01); *A61N 7/02* (2013.01); *A61B 8/00* (2013.01); *A61B 8/14* (2013.01); *A61B 2018/00464* (2013.01); *A61B 2019/5276* (2013.01); *A61H 1/00* (2013.01); *A61H 7/001* (2013.01); *A61H 2201/10* (2013.01); *A61H 2201/5007* (2013.01);
(Continued)

(58) Field of Classification Search
CPC ..................... A61B 8/00; A61B 18/14; A61B 2018/00464; A61H 1/00; A61H 2201/10; A61H 7/001; A61H 2207/00
USPC .................................. 600/407–480; 601/1–3
See application file for complete search history.

(56) References Cited

U.S. PATENT DOCUMENTS 4,792,788 A * 12/1988 Kumar ............................ 341/15
5,143,063 A    9/1992 Fellner
(Continued)

FOREIGN PATENT DOCUMENTS

DE    19800416    7/1999
DE    19935455    5/2000
(Continued)

OTHER PUBLICATIONS

U.S. Appl. No. 60/809,577.
(Continued)

*Primary Examiner* — Vani Gupta
(74) *Attorney, Agent, or Firm* — Abelman, Frayne & Schwab

(57) ABSTRACT

Apparatus is provided for lipolysis and body contouring of a subject. The apparatus includes a housing adapted for placement on tissue of the subject. The apparatus also includes a plurality of acoustic elements disposed at respective locations with respect to the housing, including at least a first and a second subset of the acoustic elements, wherein the first subset is configured to transmit energy in a plane defined by the housing, such that at least a portion of the transmitted energy reaches the second subset. Other embodiments are also described.

19 Claims, 4 Drawing Sheets

(51) Int. Cl.
*A61B 8/08* (2006.01)
*A61N 7/02* (2006.01)
*A61H 7/00* (2006.01)
*A61B 8/14* (2006.01)
*A61B 18/00* (2006.01)
*A61B 19/00* (2006.01)
*A61N 7/00* (2006.01)

(52) U.S. Cl.
CPC ..... *A61H 2207/00* (2013.01); *A61N 2007/0008* (2013.01)

(56) References Cited

U.S. PATENT DOCUMENTS

| | | | |
|---|---|---|---|
| 5,143,073 A | 9/1992 | Dory | |
| 5,175,709 A | 12/1992 | Slayton | |
| 5,178,134 A | 1/1993 | Vago | |
| 5,269,297 A | 12/1993 | Weng | |
| 5,275,165 A | 1/1994 | Ettinger et al. | |
| 5,601,526 A | 2/1997 | Chapelon et al. | |
| 5,618,275 A | 4/1997 | Bock | |
| 5,620,479 A | 4/1997 | Diederich | |
| 5,671,747 A * | 9/1997 | Connor | 600/459 |
| 5,725,482 A | 3/1998 | Bishop | |
| 5,817,018 A * | 10/1998 | Ohtomo | 600/437 |
| 5,827,204 A | 10/1998 | Grandia et al. | |
| 5,997,478 A * | 12/1999 | Jackson et al. | 600/437 |
| 6,050,943 A * | 4/2000 | Slayton et al. | 600/439 |
| 6,071,239 A | 6/2000 | Cribbs et al. | |
| 6,113,558 A | 9/2000 | Rosenschein et al. | |
| 6,128,523 A * | 10/2000 | Bechtold et al. | 600/411 |
| 6,221,019 B1 | 4/2001 | Kantrovich | |
| 6,315,741 B1 | 11/2001 | Martin et al. | |
| 6,350,276 B1 | 2/2002 | Knowlton | |
| 6,406,429 B1 | 6/2002 | Bar-Cohen et al. | |
| 6,432,067 B1 | 8/2002 | Martin et al. | |
| 6,443,901 B1 * | 9/2002 | Fraser | 600/459 |
| 6,450,979 B1 | 9/2002 | Miwa et al. | |
| 6,468,215 B1 | 10/2002 | Sarvazyan | |
| 6,470,216 B1 | 10/2002 | Knowlton | |
| 6,500,141 B1 | 12/2002 | Irion et al. | |
| 6,517,499 B1 | 2/2003 | Pereira | |
| 6,524,250 B1 | 2/2003 | Weber et al. | |
| 6,533,775 B1 | 3/2003 | Rizoiu | |
| 6,544,259 B1 | 4/2003 | Tsaliovich | |
| 6,576,875 B1 | 6/2003 | Kleffner et al. | |
| 6,577,042 B2 | 6/2003 | Lee | |
| 6,599,256 B1 * | 7/2003 | Acker et al. | 601/2 |
| 6,607,498 B2 | 8/2003 | Eshel | |
| 6,626,854 B2 | 9/2003 | Friedman et al. | |
| 6,645,162 B2 | 11/2003 | Friedman et al. | |
| 6,685,639 B1 * | 2/2004 | Wang et al. | 600/439 |
| 6,730,034 B1 | 5/2004 | Lang et al. | |
| 6,860,852 B2 | 3/2005 | Schnenberger | |
| 6,971,994 B1 | 12/2005 | Young et al. | |
| 7,110,825 B2 | 9/2006 | Vaynberg | |
| 7,112,173 B1 | 9/2006 | Kantrovich | |
| 7,250,047 B2 | 7/2007 | Anderson et al. | |
| 7,258,674 B2 | 8/2007 | Cribbs | |
| 7,273,459 B2 | 9/2007 | Desilets | |
| 7,282,047 B2 | 10/2007 | Zimmerman | |
| 7,311,679 B2 | 12/2007 | Desilets | |
| 7,331,951 B2 | 2/2008 | Eshel | |
| 7,347,855 B2 | 3/2008 | Eshel | |
| 7,399,284 B2 | 7/2008 | Miwa | |
| 7,473,224 B2 | 1/2009 | Makin | |
| 7,533,571 B2 * | 5/2009 | Ariav et al. | 73/597 |
| 7,559,905 B2 | 7/2009 | Kagosaki | |
| 7,828,734 B2 | 11/2010 | Azhari et al. | |
| 8,376,946 B2 * | 2/2013 | Littrup et al. | 600/437 |
| 2002/0045850 A1 | 4/2002 | Rowe et al. | |
| 2002/0082589 A1 * | 6/2002 | Friedman et al. | 606/1 |
| 2002/0193831 A1 | 12/2002 | Smith | |
| 2003/0065264 A1 | 4/2003 | Tsoref | |
| 2003/0083536 A1 | 5/2003 | Eshel et al. | |
| 2003/0171701 A1 * | 9/2003 | Babaev | 601/3 |
| 2004/0034340 A1 | 2/2004 | Biscup | |
| 2004/0039312 A1 | 2/2004 | Hillstead et al. | |
| 2004/0210135 A1 | 10/2004 | Hynynen et al. | |
| 2004/0215110 A1 | 10/2004 | Kreindel | |
| 2004/0217675 A1 | 11/2004 | Desilets et al. | |
| 2004/0254470 A1 * | 12/2004 | Drinkwater et al. | 600/459 |
| 2004/0267234 A1 | 12/2004 | Heart et al. | |
| 2005/0010203 A1 | 1/2005 | Edwards et al. | |
| 2005/0020921 A1 * | 1/2005 | Glassell et al. | 600/463 |
| 2005/0049543 A1 | 3/2005 | Anderson et al. | |
| 2005/0154295 A1 | 7/2005 | Quistgaard et al. | |
| 2005/0154308 A1 | 7/2005 | Quistgaard et al. | |
| 2005/0154309 A1 | 7/2005 | Etchells et al. | |
| 2005/0154313 A1 | 7/2005 | Desilets et al. | |
| 2005/0154314 A1 | 7/2005 | Quistgaard et al. | |
| 2005/0154431 A1 | 7/2005 | Quistgaard et al. | |
| 2005/0187463 A1 | 8/2005 | Quistgaard et al. | |
| 2005/0187495 A1 | 8/2005 | Quistgaard et al. | |
| 2005/0193451 A1 | 9/2005 | Quistgaard et al. | |
| 2005/0245829 A1 * | 11/2005 | Wakabayashi | 600/459 |
| 2005/0261584 A1 | 11/2005 | Eshel et al. | |
| 2006/0009753 A1 | 1/2006 | Fjield et al. | |
| 2006/0036300 A1 | 2/2006 | Kreindel | |
| 2006/0037392 A1 * | 2/2006 | Carkner et al. | 73/290 V |
| 2006/0047281 A1 | 3/2006 | Kreindel | |
| 2006/0094988 A1 | 5/2006 | Tosaya et al. | |
| 2006/0096594 A1 | 5/2006 | Bonney et al. | |
| 2006/0100550 A1 | 5/2006 | Schultheiss et al. | |
| 2006/0122509 A1 | 6/2006 | Desilets et al. | |
| 2006/0158956 A1 | 7/2006 | Laugharn et al. | |
| 2006/0184024 A1 * | 8/2006 | Da Silva et al. | 600/438 |
| 2006/0184071 A1 | 8/2006 | Klopotek | |
| 2006/0189976 A1 | 8/2006 | Karni | |
| 2006/0211958 A1 | 9/2006 | Rosenberg | |
| 2007/0004984 A1 | 1/2007 | Crum et al. | |
| 2007/0066897 A1 | 3/2007 | Sekins et al. | |
| 2007/0083120 A1 | 4/2007 | Cain et al. | |
| 2007/0106157 A1 | 5/2007 | Kaczkowski et al. | |
| 2007/0161902 A1 | 7/2007 | Dan | |
| 2007/0179365 A1 * | 8/2007 | Bitton et al. | 600/310 |
| 2007/0239074 A1 | 10/2007 | Ein-Gal et al. | |
| 2007/0239075 A1 | 10/2007 | Rosenberg et al. | |
| 2007/0265610 A1 | 11/2007 | Thapliyal et al. | |
| 2008/0045865 A1 | 2/2008 | Kislev | |
| 2008/0051656 A1 | 2/2008 | Vaezy et al. | |
| 2008/0058682 A1 | 3/2008 | Azhari et al. | |
| 2008/0076958 A1 | 3/2008 | Britva | |
| 2008/0146970 A1 | 6/2008 | Litman et al. | |
| 2008/0177180 A1 * | 7/2008 | Azhari et al. | 600/439 |
| 2008/0183167 A1 | 7/2008 | Britva | |
| 2008/0195036 A1 | 8/2008 | Merchant et al. | |
| 2008/0234609 A1 | 9/2008 | Kreindel | |
| 2008/0269163 A1 | 10/2008 | Sostaric et al. | |
| 2009/0012585 A1 | 1/2009 | Karni | |
| 2009/0076420 A1 | 3/2009 | Kreindel | |
| 2009/0171424 A1 | 7/2009 | Britva | |
| 2009/0192506 A9 | 7/2009 | Vaska et al. | |
| 2009/0221938 A1 | 9/2009 | Rosenberg | |
| 2009/0227910 A1 | 9/2009 | Pedersen et al. | |
| 2009/0247912 A1 | 10/2009 | Warnking | |
| 2009/0254068 A1 | 10/2009 | Karni | |
| 2009/0326437 A1 | 12/2009 | Beerwerth et al. | |
| 2010/0036292 A1 | 2/2010 | Darlington et al. | |
| 2010/0049178 A1 | 2/2010 | Deem et al. | |
| 2011/0167640 A1 | 7/2011 | Flyash et al. | |

FOREIGN PATENT DOCUMENTS

| | | |
|---|---|---|
| WO | WO 00/53263 | 9/2000 |
| WO | WO 2005/074365 | 8/2005 |
| WO | WO 2005/112807 | 12/2005 |
| WO | WO 2005/112815 | 12/2005 |
| WO | WO 2006/018837 | 2/2006 |
| WO | WO 2006/122136 | 11/2006 |
| WO | WO 2007/009118 | 1/2007 |
| WO | WO 2008/123951 | 10/2008 |
| WO | 2013111139 A1 | 8/2013 |

(56) References Cited

FOREIGN PATENT DOCUMENTS

OTHER PUBLICATIONS

U.S. Appl. No. 60/780,772.
U.S. Appl. No. 60/860,635.
Moran CM et al., "Ultrasonic propagation properties of excised human skin", Ultrasound Med Biol. 21(9):1177-90, 1995.
Akashi N et al., "Acoustic properties of selected bovine tissue in the frequency range 20-200MHz", J Acoust Soc Am. 98(6):3035-9, 1995.
An International Preliminary Report dated May 11, 2010, which issued during the prosecution of Applicant's PCT/IL08/001390.
An International Search Report dated Jan. 25, 2010, which issued during the prosecution of Applicant's PCT/IL09/00893.
An International Search Report dated Jan. 25, 2010, which issued during the prosecution of Applicant's PCT/IL09/00894.
An Office Action dated May 20, 2011, which issued during the prosecution of Applicant's U.S. Appl. No. 12/207,043.
Communication together with annex to the communication both dated Apr. 13, 2011 which issued during the prosecution of Applicant's European App No. 07713327.0.
Office Action dated Sep. 17, 2010 received in U.S Appl. No. 12/207,043.
Office Action dated Dec. 30, 2011 in U.S. Appl. No. 12/207,043.
Office Action dated Apr. 9, 2012 in U.S. Appl. No. 12/682,748.
International Search Report dated Oct. 26, 2011 issued in PCT Patent Application No. PCT/IL11/00382.
International Search Report dated May 20, 2013 issued in PCT Patent Application No. PCT/IL2013/050071.
Office Action dated Jul. 11, 2013, issued during prosecution of Applicant's U.S. Appl. No. 13/063,567.
An International Search Report dated May 8, 2012, which issued during the prosecution of Applicant's PCT Patent Application No. PCT/IL2011/000942 (ISR attached).

\* cited by examiner

US 9,107,798 B2

METHOD AND SYSTEM FOR LIPOLYSIS AND BODY CONTOURING

CROSS-REFERENCES TO RELATED APPLICATIONS

This application is a continuation-in-part of a U.S. non-provisional patent application, filed by Azhari et al. on Jan. 8, 2007, Ser. No. 11/651,198, entitled, "A device for ultrasound monitored tissue treatment," and claims the priority of:

U.S. Provisional Patent Application 60/780,772 to Azhari et al., filed Mar. 9, 2006, entitled, "A method and system for lypolysis and body contouring,"

U.S. Provisional Patent Application 60/809,577 to Azhari et al., filed May 30, 2006, entitled, "A device for ultrasound monitored tissue treatment," and U.S. Provisional Patent Application 60/860,635 to Azhari et al., filed Nov. 22, 2006, entitled, "Cosmetic tissue treatment using ultrasound."

Each of the above applications is incorporated herein by reference.

FIELD OF THE INVENTION

The present invention relates in general to tissue treatment by application of energy thereto, and specifically to the monitoring and applying of ultrasound to skin.

BACKGROUND OF THE INVENTION

Systems for applying energy to biological tissue are well known. Such energy application may be intended to heal injured tissue, ablate tissue, or improve the appearance of tissue. Energy may be applied in different forms, such as radiofrequency, laser, or ultrasound.

PCT Publication WO 06/080012 to Kreindel, which is incorporated herein by reference, describes a system and method for heating a tissue volume under a skin surface of an individual from an initial temperature to a predetermined treatment temperature in the range of 42 C-60 C. The method is described as comprising applying electrodes to the skin surface and providing from the electrodes a continuous wave radiofrequency (RF) energy or a quasi-continuous wave RF energy, where the RF energy has a power selected to heat the tissue volume to the final temperature in an amount of time exceeding 0.5 sec. The system is described as comprising electrodes and an RF generator configured to provide a continuous wave RF voltage energy or a quasi-continuous wave RF voltage across the electrodes where the RF energy has a power selected to heat the tissue volume to the final temperature in an amount of time exceeding 0.5 sec.

US Patent Application Publication 2004/0039312 to Hillstead et al., which is incorporated herein by reference, describes a system for the destruction of adipose tissue utilizing high intensity focused ultrasound (HIFU) within a patient's body. The system is described as comprising a controller for data storage and the operation and control of a plurality of elements. One element is described as a means for mapping a human body to establish three dimensional coordinate position data for existing adipose tissue. The controller is able to identify the plurality of adipose tissue locations on said human body and establish a protocol for the destruction of the adipose tissue. A HIFU transducer assembly having one or more piezoelectric element(s) is used along with at least one sensor, wherein the sensor provides feedback information to the controller for the safe operation of the piezoelectric element(s). The sensor is electronically coupled to the controller, and the controller provides essential treatment command information to one or more piezoelectric element(s) based on positioning information obtained from the three dimensional coordinate position data.

U.S. Pat. No. 6,500,141 to Irion et al., which is incorporated herein by reference, describes an apparatus for treating body tissue, in particular superficial soft tissue, with ultrasound, comprising an ultrasonic generation unit and an applicator, by means of which the ultrasound can be irradiated from an applicator surface facing the body surface from outside through the body surface into the body tissue. A suction apparatus for sucking in the body surface against the applicator surface is provided. An apparatus for treating body tissue including superficial soft tissue, with ultrasound, is described as comprising an ultrasonic generation unit and an applicator having an applicator surface facing the body surface from which the ultrasound can be irradiated through the body surface into the body tissue. A suction apparatus is provided for taking in the body surface against the applicator surface which is curved inwardly.

U.S. Pat. No. 5,601,526 to Chapelon et al., which is incorporated herein by reference, describes a method and apparatus for performing therapy using ultrasound. The apparatus is described as using a treatment device having at least one piezoelectric transducer element to supply ultrasonic waves focused onto a focal point or region that determines the tissue zone submitted to therapy. The treatment device, which is controlled by a control device, supplies two types of ultrasonic waves, the first one being thermal waves that produce a predominantly thermal effect on the tissue being treated and the second one being cavitation waves that produce a predominantly cavitation effect on the tissue to be treated. A therapy method is described, using ultrasound for the purpose of destroying a target. The target includes tissue, which may be located inside a body of a mammal. Ultrasonic waves are focused onto a focal point or region. A tissue zone to be submitted to the therapy is determined. Ultrasonic waves are supplied to the target. The ultrasonic waves of two types: thermal waves, for producing a predominantly thermal effect on tissue to be treated, and cavitation waves, for producing a predominantly cavitation effect on the tissue to be treated. The two types of waves are applied for a time sufficient to effect therapy by destroying at least a portion of the tissue, and the thermal ultrasonic waves are supplied at least at a beginning of treatment. In an embodiment, the ultrasonic waves are supplied after an adjustable predetermined time interval for allowing preheating of the tissue to be treated.

PCT Publication WO 06/018837 to Azhari et al., which is incorporated herein by reference, describes a method of damaging a target tissue of a subject. The method is described as comprising: (a) imaging a region containing the target tissue; (b) determining a focal region of a damaging radiation; (c) positioning the focal region onto the target tissue; and (d) damaging the target tissue by an effective amount of the damaging radiation. The determination of the focal region is described by delivering to the region bursts of ultrasonic radiation from a plurality of directions and at a plurality of different frequencies, and passively scanning the region so as to receive from the region ultrasonic radiation having at least one frequency other than the plurality of different frequencies.

US Patent Application Publications 2005/0154308, 2005/0154309, 2005/0193451, 2004/0217675, 2005/0154295, 2005/0154313, 2005/0154314, 2005/0154431, 2005/0187463, 2005/0187495, 2006/0122509, 2003/0083536, 2005/0261584, 2004/0215110, 2006/0036300, 2002/0193831, and 2006/0094988, U.S. Pat. Nos. 5,143,063, 6,730,034, 6,450,979, 6,113,558, 6,607,498, 6,626,854, 6,645,162, and 6,971,994, and PCT Patent Publications WO/2000/053263, and WO/2005/074365 are incorporated herein by reference.

The following articles, which are incorporated herein by reference, may be of interest:

Moran C M et al., "Ultrasonic propagation properties of excised human skin," Ultrasound Med Biol. 21(9):1177-90 (1995)

Akashi N et al., "Acoustic properties of selected bovine tissue in the frequency range 20-200 MHz," J Acoust Soc Am. 98(6):3035-9 (1995)

SUMMARY OF THE INVENTION

In some embodiments of the invention, cosmetic and/or medical apparatus is provided which comprises a system for lipolysis and body contouring, comprising a tissue monitoring system and a tissue treatment system. The monitoring system assesses a state of tissue of a subject, and the treatment system applies a treatment to the tissue. The treatment includes body contouring, specifically by lipolysis. Typically, the monitoring and treatment occur in alternation, until the monitoring system determines that the treatment has been completed. For some applications, one of the systems comprises a housing, and the tissue of the subject is surrounded at least partially by the housing, to allow the system to monitor or treat (as appropriate) the tissue. In this case, the system typically transmits ultrasound energy that is designated to remain in large part within the housing and tissue therein, and generally not to affect tissue outside of the housing.

As appropriate for a given application, the system comprising the housing may be the monitoring system, the treatment system, or both the monitoring system and the treatment system.

In an embodiment, a first subset of the plurality of acoustic elements is disposed at one location of the housing and a second subset of acoustic elements is disposed at a second location of the housing. Each subset contains one or more acoustic elements designated to transmit energy and/or one or more acoustic elements designated to receive and/or reflect energy. The acoustic elements configured to receive energy comprise transducers which convert the energy into information capable of being processed by a processor typically located remotely from the acoustic elements, enabling reflected, scattered, or through-transmitted energy to be analyzed.

In some embodiments, the housing comprises two generally-parallel cylinders spaced at a predetermined distance from one another so as to define a plane between the cylinders, and a support element connected to both cylinders. For some applications, an electromechanical device is configured to vary the distance between the cylinders and/or rotate the cylinders after the housing comes in contact with skin of the subject. Consequently, the tissue is pinched and drawn at least partially into the plane to be subsequently monitored or treated (as appropriate) by the acoustic elements. In this case, the system typically transmits ultrasound energy that is designated to remain in large part within the housing and tissue therein, and generally not to affect tissue outside of the housing. The acoustic elements are typically disposed such that they are optimized to receive ultrasound energy coming generally from within the plane.

For some applications, the housing comprises a flexible cuff configured to surround a limb of the subject designated for treatment. The subsets of acoustic elements are typically arranged around the cuff on a circle defined by the cuff. For some applications, the acoustic elements are configured to remain fixed at their respective locations with respect to the cuff, while the cuff moves about the limb. For other applications, an electromechanical device moves at least a portion of the acoustic elements to different locations on the cuff.

Treatments using the treatment system may include, as appropriate, causing heating, tissue damage, thermal ablation, mechanical irritation, cell structure alteration, augmented diffusion, and/or a cavitation effect. Typically, the treatment system comprises circuitry for configuring the applied energy as high intensity focused ultrasound (HIFU), using techniques known in the art.

In an embodiment, the monitoring system generally continuously generates acoustic maps or images depicting changes occurring during a treatment of the tissue within the housing. For some applications, this allows an operator of the treatment system to monitor the progress of a treatment, and to alter a parameter of the treatment in response thereto. Such a parameter may include, for example, a location of a focus of the HIFU, a positioning of the housing on the subject's skin, or a strength of the applied energy. Alternatively or additionally, the treatment system and monitoring system operate in a closed loop fashion, whereby an output of the monitoring system (e.g., a location of fatty tissue) is used as an input parameter to the treatment system, such that the treatment system can adjust its operating parameters in response to the output of the monitoring system (and, for example, heat the fatty tissue).

In an embodiment, the apparatus comprises a tracking system comprising reference sensors configured to track progress of treatments conducted on different days, or during the same procedure, by registering and recording the spatial location of the treated tissue. Typically, the spatial localization is achieved in comparison to corresponding predefined anatomical locations of the subject with respect to the housing. Alternatively, the spatial localization corresponds to coordinates in a room with respect to the housing.

There is therefore provided, in accordance with an embodiment of the present invention, apparatus including:

A housing adapted for placement on tissue of a subject; and a plurality of acoustic elements disposed at respective locations with respect to the housing, including at least a first and a second subset of the acoustic elements, the first subset is configured to transmit energy in a plane defined by the housing, such that at least a portion of the transmitted energy reaches the second subset.

In an embodiment, at least one of the acoustic elements of the second subset includes an ultrasound reflector.

In an embodiment, the tissue includes skin of the subject, and the first subset is configured to transmit the energy through the skin.

In an embodiment, the housing is flexible at least in part, and configured to flex to match the shape of the tissue.

In an embodiment, the housing is generally rigid.

In an embodiment, the apparatus includes a source of suction configured to draw the tissue into the housing, and the plurality of acoustic elements are disposed with respect to the housing so as to direct the energy to the tissue within the housing.

In an embodiment, the housing is configured to pinch a portion of the tissue to draw the portion into the plane.

In an embodiment, the first subset is configured to substantially avoid transmitting energy out of the plane.

In an embodiment, the first subset includes ultrasound transducers.

In an embodiment, at least one of the acoustic elements of the second subset includes an ultrasound transducer.

In an embodiment, the ultrasound transducer is configured to transmit energy in the plane, such that at least a portion of the energy transmitted by the ultrasound transducer reaches the first subset.

In an embodiment, the first subset is configured to transmit treatment energy.

In an embodiment, the first subset is configured to configure the treatment energy for lipolysis of adipose tissue.

In an embodiment, the first subset is configured to apply the treatment energy to the tissue by elevating a temperature of the tissue by less than 10 C.

In an embodiment, the first subset is configured to elevate the temperature by less than 5 C.

In an embodiment, the apparatus includes an electromechanical device configured to move at least some of the plurality of acoustic elements with respect to the plane.

In an embodiment, in moving the elements, the electromechanical device is configured to move at least a portion of the acoustic elements of one of the subsets at the same time.

In an embodiment, the housing includes the electromechanical device.

In an embodiment, the electromechanical device is configured to move the housing.

In an embodiment, the electromechanical device is configured to maintain a predetermined distance between the first subset and the second subset.

In an embodiment, the electromechanical device is configured to vary a distance between the first subset and the second subset.

In an embodiment, the electromechanical device is configured to draw the tissue into the housing by pinching the tissue, and the plurality of acoustic elements are disposed with respect to the housing so as to direct the energy to the tissue within the housing.

In an embodiment, the plurality of acoustic elements are configured to monitor a parameter of the tissue.

In an embodiment, the parameter of the tissue includes fat content.

In an embodiment, a first portion of the plurality of acoustic elements is configured to transmit treatment energy, and at least some of the plurality of acoustic elements are configured to monitor an alteration of the parameter in response to the treatment energy.

In an embodiment, the apparatus includes an energy source that is not an acoustic element from the first or second subsets of acoustic elements, and the energy source is configured to transmit treatment energy in response to the monitoring.

In an embodiment, the energy source is configured to configure the treatment energy for lipolysis of adipose tissue.

In an embodiment, the energy source is configured to transmit treatment energy in conjunction with the monitoring.

In an embodiment, the energy source is configured to apply the treatment to the tissue by elevating a temperature of the tissue by less than 10 C.

In an embodiment, the energy source is configured to elevate the temperature by less than 5 C.

In an embodiment, the housing includes a cuff, and the plurality of acoustic elements are coupled to the cuff.

In an embodiment, the plurality of acoustic elements are disposed with respect to the cuff so as to define a ring of acoustic elements.

In an embodiment, the tissue includes tissue of a limb of the subject, and the cuff is configured to surround the limb.

In an embodiment, the apparatus includes a motor coupled to the cuff, configured to move at least some of the plurality of acoustic elements.

In an embodiment, the plurality of acoustic elements are disposed at fixed locations with respect to the cuff.

In an embodiment. the plurality of acoustic elements is configured to effect contouring of the body of the subject.

In an embodiment, the apparatus includes a sensor coupled to the housing, configured to identify a location of the housing.

In an embodiment, the apparatus includes a sensor coupled to the housing, configured to identify a location of tissue, and a processing unit, configured to compare the location with a previously-stored location of tissue.

There is additionally provided, in accordance with an embodiment of the present invention, apparatus, including:

a cuff housing configured to surround a portion of a limb of a subject; and a plurality of acoustic elements disposed at respective locations with respect to the cuff housing, including at least a first and a second subset of the acoustic elements, the first subset is configured to transmit energy such that at least a portion of the transmitted energy reaches the second subset.

In an embodiment, the plurality of acoustic elements are disposed with respect to the cuff housing so as to define a ring of acoustic elements.

In an embodiment, the plurality of acoustic elements are disposed at fixed locations with respect to the cuff housing.

In an embodiment, at least one of the acoustic elements of the second subset includes an ultrasound reflector.

In an embodiment, the cuff housing is flexible at least in part, and configured to flex to match the shape of the portion of the limb.

In an embodiment, the cuff housing is generally rigid.

In an embodiment, the first subset includes ultrasound transducers.

In an embodiment, at least one of the acoustic elements of the second subset includes an ultrasound transducer.

In an embodiment, the portion of the limb includes skin of the subject, and the ultrasound transducer is configured to transmit energy to the skin, such that at least a portion of the energy transmitted by the ultrasound transducer reaches the first subset.

In an embodiment, the first subset is configured to transmit treatment energy to the portion of the limb.

In an embodiment, the first subset is configured to configure the treatment energy for lipolysis of adipose tissue.

In an embodiment, the first subset is configured to apply the treatment energy to the portion of the limb by elevating a temperature of fat in the portion of the limb by less than 10 C.

In an embodiment, the first subset is configured to elevate the temperature by less than 5 C.

In an embodiment, the apparatus includes an electromechanical device configured to move at least some of the plurality of acoustic elements with respect to the portion of the limb.

In an embodiment, in moving the elements, the electromechanical device is configured to move at least a portion of the acoustic elements of one of the subsets at the same time.

In an embodiment, the cuff housing includes the electromechanical device.

In an embodiment, the electromechanical device is configured to move the cuff housing.

In an embodiment, the electromechanical device is configured to maintain a predetermined distance between the first subset and the second subset.

In an embodiment, the electromechanical device is configured to vary a distance between the first subset and the second subset.

In an embodiment, the plurality of acoustic elements are configured to monitor a parameter of the portion of the limb of the subject.

In an embodiment, the parameter of the portion of the limb includes fat content, and the plurality of acoustic elements are configured to monitor the fat content.

In an embodiment, a first portion of the plurality of acoustic elements is configured to transmit treatment energy, and a second portion of the plurality of acoustic elements is configured to monitor an alteration of the parameter in response to the treatment energy.

In an embodiment, the apparatus includes an energy source that is not an acoustic element from the first or second subsets of acoustic elements, and the energy source is configured to transmit treatment energy in response to the monitoring.

In an embodiment, the energy source is configured to configure the treatment energy for lipolysis of adipose tissue.

In an embodiment, the energy source is configured to transmit treatment energy in conjunction with the monitoring.

In an embodiment, the plurality of acoustic elements is configured to effect contouring of the body of the subject.

In an embodiment, the apparatus includes at least one sensor configured to track the contouring.

In an embodiment, the at least one sensor is coupled to the cuff housing.

In an embodiment, the at least one sensor is configured to localize the portion of the limb of the subject with respect to predefined locations of a body of the subject.

In an embodiment, the apparatus includes a plurality of reference elements that are configured to be disposed at respective coordinates in a room, and to be in communication with the sensor.

In an embodiment, the plurality of reference elements are configured to localize the portion of the limb of the subject with respect to the coordinates of the room.

There is also provided, in accordance with an embodiment of the present invention, apparatus, including:

a housing adapted for placement on tissue of a subject; and a plurality of energy transducers disposed at respective locations with respect to the housing, including at least a first and a second subset of the energy transducers, the first subset is configured to transmit energy in a plane defined by the housing, such that at least a portion of the transmitted energy reaches the second subset.

In an embodiment, the first subset is configured to substantially avoid transmitting energy out of the plane.

In an embodiment, the first subset is configured to emit laser energy into the plane.

In an embodiment, the first subset is configured to transmit visual energy into the plane.

In an embodiment, the first subset is configured to transmit radiofrequency energy into the plane.

In an embodiment, the first subset is configured to transmit electromagnetic radiation into the plane.

In an embodiment, the first subset is configured to transmit microwave radiation into the plane.

In an embodiment, the apparatus includes a source of suction configured to draw the tissue into the housing, and the plurality of energy transducers are disposed with respect to the housing so as to direct the energy to the tissue within the housing.

In an embodiment, the housing includes a cuff configured to surround a limb of the subject, and the plurality of energy transducers are coupled to the cuff.

In an embodiment, the first subset is configured to transmit treatment energy configured for lipolysis of adipose tissue.

In an embodiment, the first subset is configured to transmit ultrasound energy into the plane.

In an embodiment, the apparatus is configured to treat the tissue of the subject, and the apparatus is configured to monitor the treatment by transmitting ultrasound energy.

The present invention will be more fully understood from the following detailed description of embodiments thereof, taken together with the drawings, in which:

DETAILED DESCRIPTION OF EMBODIMENTS

Figure 1:
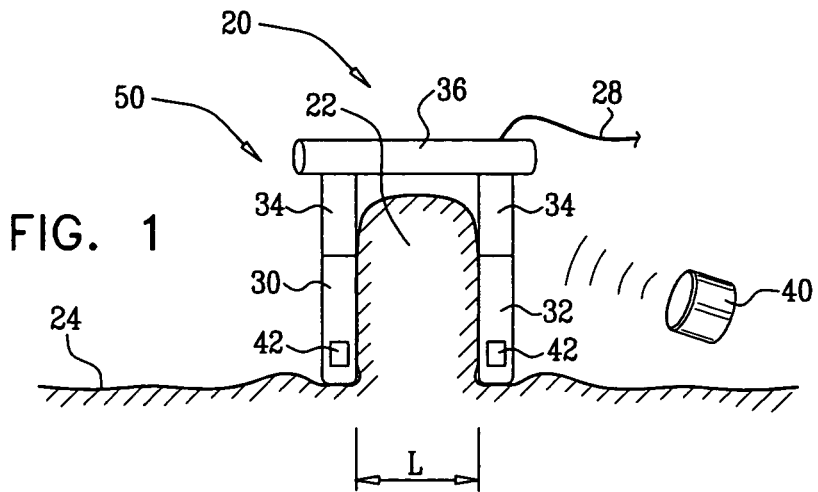
FIG. 1 is a schematic illustration of a monitoring device positioned on tissue of a subject, and a treatment device, in accordance with an embodiment of the present invention.

FIG. 1 is a schematic illustration of a system 20 for lipolysis and body contouring, comprising a housing 50, a plurality of acoustic elements comprising a subset 30 and a subset 32 of the acoustic elements, and an energy source 40, in accordance with an embodiment of the present invention. Each subset comprises one or more acoustic elements. At least a pair of acoustic elements are disposed at respective locations with respect to housing 50. Housing 50 is typically but not necessarily rigid, and comprises a support element 36 connected to ends of two cylinders 34 or members that are shaped in a different manner. In an embodiment, housing 50 is flexible, at least in part.

Subsets 30 and 32 are disposed upon cylinders 34, which are spaced at a distance L from one another. Distance L typically ranges from about 5 mm to about 150 mm, e.g., about 5 mm to 40 mm or 40 mm to 150 mm. The space between cylinders 34 defines a plane in which tissue 24 designated for treatment is drawn into housing 50. For some applications, an electromechanical device (not shown) is connected via lead 28 to support element 36 and moves cylinders 34 in a controlled motion, varying distance L between cylinders 34. When housing 50 is placed on tissue 24 designated for monitoring or treatment (as appropriate), such motion pinches and draws tissue 24 into the plane defined by housing 50. Alternatively or additionally, cylinders 34 rotate in the same direction or in opposite directions, to draw new tissue into the plane.

For some applications, the electromechanical device is disposed upon cylinders 34. For other applications, a source of suction, e.g., a vacuum pump disposed upon housing 50 draws a portion 22 of tissue 24 into housing 50.

Once tissue 24 has been drawn into housing 50, low intensity ultrasound energy used for detecting a parameter of portion 22 of tissue 24, e.g., fat content, is transmitted between first subset 30 and second subset 32. A first portion of first subset 30 transmits energy to be received, at least in part, by a first portion of second subset 32. Alternatively or additionally, a second portion of second subset 32 transmits energy to be received, at least in part, by a second portion of first subset 30. Cylinders 34 are arranged such that the energy is transmitted through portion 22 of tissue 24 and received on subset 30 and/or subset 32. Typically, tissue 24 includes skin of the subject and energy is transmitted from either subset 30 and 32, through the skin.

The electromechanical device maintains distance L between first subset 30 and second subset 32 during the monitoring and treatment process. Acoustic elements in subset 30 may be moved away from acoustic elements in subset 32 due to the movement of cylinders 34 by the electromechanical device. Alternatively or additionally, portions of the acoustic elements are moved to different locations with respect to cylinder 34. The movement and distances between the portions of the acoustic elements are typically recorded by a linear encoder or by counting steps of a stepper motor. Such recording is useful in the monitoring of the body contouring process, as described hereinbelow.

In an embodiment, the electromechanical device moves housing 50 to different locations on tissue 24 of the subject, enabling the acoustic elements to detect the presence of adipose tissue at multiple locations on tissue 24 of the subject. For some applications, moving housing 50 comprises rotating cylinders 34 along tissue 24 while periodically counter-rotating cylinders 34 such that tissue 24 is rolled between cylinders 34 and introduced within housing 50. Alternatively or additionally, the rolling of the cylinders is configured to induce a form of peristaltic motion of tissue 24. For other applications, the electromechanical device is not used to move housing 50 along tissue 24 of the subject.

Upon detection of the presence of adipose tissue, an independent energy source 40, that is not an acoustic element from subsets 30 and 32, applies treatment energy to portion 22 of tissue 24. Energy source 40 is coupled to housing 50 (configuration not shown), or, alternatively, mechanically separate from the housing. Energy source 40 comprises circuitry for focusing energy designated for the destruction of adipose tissue, such as acoustic energy (e.g., high intensity focused ultrasound, shock waves, sharp negative pressure pulses, or high intensity ultrasound waves), electromagnetic radiation (e.g., microwave radiation), laser energy, and/or visual or near-visual energy (e.g., infra-red). Energy source 40 transmits energy intense enough to cause damage to adipose tissue within portion 22. Effects of treatments by energy source 40 may include, as appropriate, heating, tissue damage, thermal ablation, mechanical irritation, cell structure alteration, augmented diffusion, and/or a cavitation effect. For some applications, lipolysis is accomplished when energy source 40 elevates the temperature of portion 22 of tissue 24 by less than 10 C, e.g., less than 5 C.

Energy source 40 transmits treatment energy in conjunction with the monitoring of the treatment process by acoustic subsets 30 and 32. For some applications, in addition to monitoring the treatment procedure, the body contouring process is tracked by sensors 42. For example, sensors 42 may comprise electromagnetic sensors or optical sensors that are coupled to housing 50. The sensed information is transmitted to a processing unit. Storing the tracking information allows for improved follow-up and comparison of body contouring treatments conducted on different days or during the treatment.

For some applications, tracking the treatment process occurs in conjunction therewith. In response to an indication of fat content detected by the acoustic elements in a particular area of the body of the subject, the physician marks the area, designating it for treatment. Housing 50 is subsequently placed on the designated area to provide treatment and monitoring thereof. Following the treatment, housing 50 is repositioned in the designated area to enable tracking of the body contouring process by sensors 42. Sensors 42 help ensure that (1) treatment has been applied to all subsections of the designated area and/or (2) treatment has not been applied multiple times to the same subsection during a single session. Thus, for some applications, treatment locations during one session are stored to facilitate the initiation of treatments in subsequent locations other than already-treated regions.

Through-transmitted and scattered waves are received by at least a portion of the acoustic elements. In some cases, the received waves are reflected from some acoustic elements towards other acoustic elements, which transfer information representing the detection of adipose tissue and subsequent monitoring of the treatment procedure to a processor (not shown). In an embodiment, the processor displays the information representing the detection by the acoustic elements, as well as provides on-line monitoring during the use of system 20.

Typically, monitoring by the acoustic elements is accomplished by a series of low intensity ultrasonic pulses transmitted from a portion of acoustic elements of subset 30. It is to be noted that other waveforms can be utilized. The energy is scattered by, reflected by, or transmitted through portion 22 of tissue 24. At least a portion of the energy is then received by subset 32, which is designated for monitoring the procedure. This portion of the energy is received by a portion of the acoustic elements of subset 32, and travel times of pulses between subset 30 and 32 ($T_1$) are calculated, using techniques known in the art. The amplitudes ($Amp_1$) of echoes received by the portion of the acoustic elements of subset 32 are also registered.

In like manner, for some applications, energy is transmitted from portions of the acoustic elements of subset 32 to be received and registered by portions of the acoustic elements of subset 30.

The average speed of sound (SOS) is calculated as follows:

$SOS = L/T_1$, where L represents the distance between subsets 30 and 32. Distance L is recorded by a linear encoder, a stepper motor or another device known in the art and configured to sense and digitize linear position change for position measurement and feedback to the monitoring system, in order to calculate and monitor the SOS.

The average attenuation coefficient (mu) is calculated as follows:

$$mu = \mathrm{Log}(Amp_1/Amp_0),$$

where $Amp_0$ is a reference amplitude.

In addition, the spectrum of both reflected waves ($S_R$) and the spectrum of the transmitted waves ($S_T$) are analyzed.

Using the properties SOS, mu, $S_R$ and $S_T$, portion 22 of tissue 24 is characterized to assess whether the concentration of fat in portion 22 is sufficient for application of treatment energy thereto. Once treatment energy has been applied to portion 22, changes in the properties of SOS, mu, $S_R$ and $S_T$ are monitored. Expected changes as a result of the treatment process (e.g., elevated temperature, appearance of cavitation bubbles, and changes in the cellular structure) are manifested in and alter the acoustic properties SOS, mu, $S_R$ and $S_T$. For example, it is known that SOS and mu change with temperature, and that the appearance of cavitation bubbles induces half harmonic signals in the spectrum relating to the reflected and transmitted waves. Methods described herein may be practiced in combination with methods for assessing a parameter of tissue described in the above-mentioned articles by Moran et al. and Akashi et al.

The portion of the acoustic elements of subset 32 which receive the scattered and through-transmitted echoes comprise transducers that are typically connected to a processing unit of a workstation (not shown). The workstation is configured to drive and receive data from the transducers. The workstation processes signals from the transducers in order to generate acoustic maps or images (e.g., a local B-scan image generated by the echoes or an image generated by through-transmission) of portion 22 of tissue 24 that is enclosed in the plane. The resulting maps or images indicate whether a desired extent of treatment has been obtained (e.g., a level of damage to tissue 24) and guide further treatment. Cycles of treatment and monitoring occur in a generally closed-loop manner and are repeated using different signaling parameters, until a sufficient amount of data is collected. Maps of acoustic properties or images of the tissue are reconstructed, typically using algorithms known in the art. As appropriate, the maps or images may depict various acoustic properties of the tissue, such as reflectivity, speed of sound, attenuation, acoustic impedance, and other properties. For some applications, the maps or images thus acquired are saved for later use as a reference set.

It is to be noted that since tissue 24 to be treated includes adipose tissue, for some applications the registered information is calibrated to provide tables relating the intensity of treatment to the expected changes in each of the acoustic properties: SOS, mu, $S_R$ and $S_T$. When the desired effect has been achieved, the treatment is terminated.

Figure 2A:
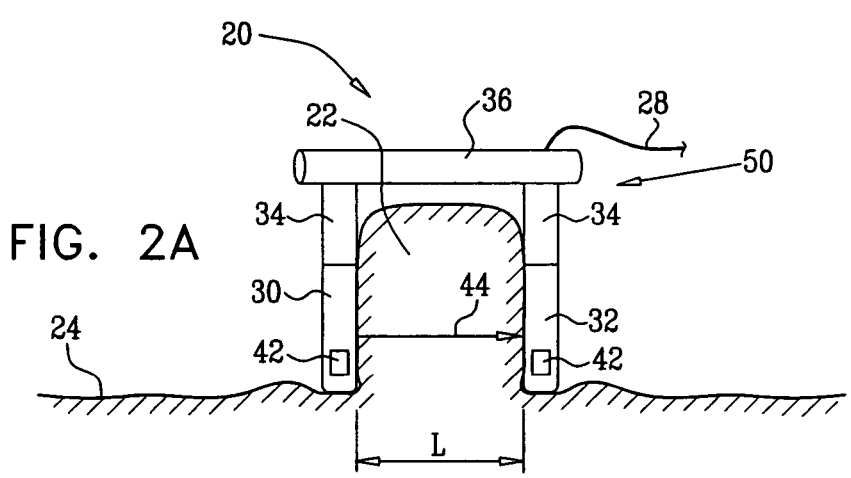
FIGS. 2A and 2B are schematic illustrations of the monitoring device of FIG. 1 comprising the treatment device, in accordance with respective embodiments of the present invention.

Reference is now made to FIG. 2A, which is a schematic illustration of system 20, in accordance with another embodiment of the present invention. Acoustic elements detect the presence of fat and monitor the body contouring process as described hereinabove with reference to FIG. 1. Subset 30 transmits the treatment energy to portion 22 of tissue 24 (as indicated by arrow 44). Subset 30 and/or 32 serves as a monitor and transmits signals for assessing the condition of portion 22 clamped between cylinders 34. Treatment by subset 30 is similar to the treatment effected by energy source 40, described hereinabove with reference to FIG. 1. Subset 30 and subset 32 work in conjunction with each other in a generally closed-loop operation cycling repeatedly between (a) subset 30 applying a treatment to portion 22 of tissue 24 in response to the monitored state of portion 22, and (b) subset 30 and/or 32 monitoring the state of portion 22 of tissue 24 following (a).

Figure 2B:
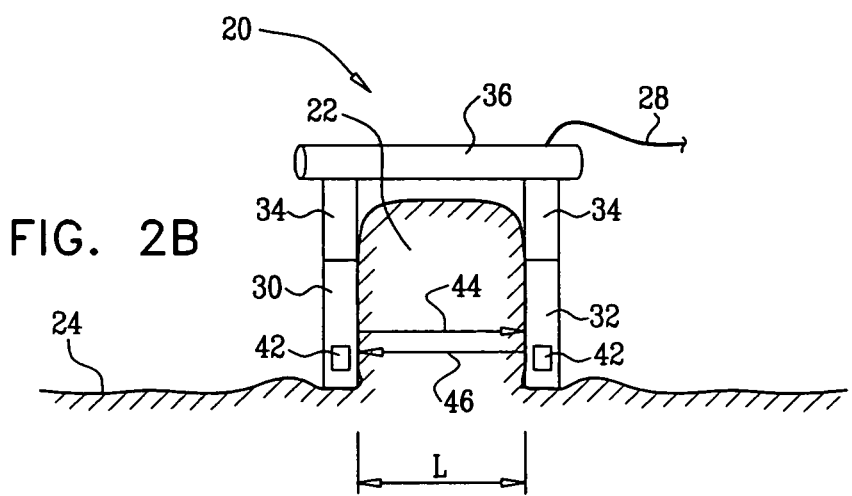

Reference is now made to FIG. 2B, which is a schematic illustration of system 20 of FIG. 2A with the exception that a first portion of acoustic elements of subset 32 transmits treatment energy (as indicated by arrow 46) in combination with the treatment energy transmitted by a first portion of the acoustic elements of subset 30 (as indicated by arrow 44), in accordance with an embodiment of the present invention. For some applications, portions of subsets 30 and 32 are activated simultaneously to generate a standing wave in the plane. The intensity peak of such a wave is located between subsets 30 and 32, and its frequency and amplitude are suitable for treating portion 22 of tissue 24. The same or other portions of subsets 30 and 32 monitor waves transmitted through or reflected from portion 22, typically between successive treatments by subsets 30 and 32.

Figure 3:
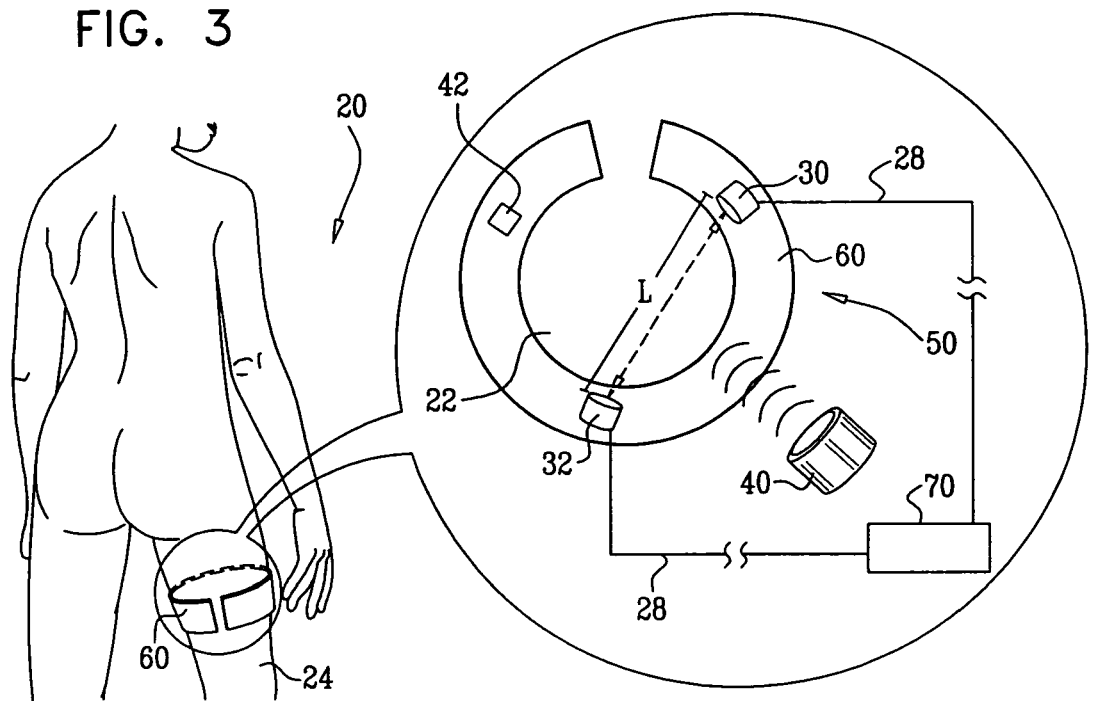
FIG. 3 is a schematic illustration of a monitoring device positioned on tissue of a subject and a treatment device, in accordance with another embodiment of the present invention.

Reference is now made to FIG. 3, which is a schematic illustration of system 20 as described hereinabove with reference to FIG. 1, with the exception that housing 50 comprises a cuff 60, in accordance with an embodiment of the present invention. Cuff 60 is typically but not necessarily flexible and is designed to surround a limb of the subject. For some applications, cuff 60 comprises a water bag that is designed to surround the limb to be treated. A plurality of acoustic elements are disposed with respect to cuff 60 so as to define a ring. In an embodiment, the "ring" comprises only two acoustic elements. Typically, the plurality of acoustic elements comprises between 2 and 64, e.g., 2 to 12, acoustic elements. Ultrasound waves are transmitted from a portion of acoustic elements of subset 30 through the limb and are received by a portion of acoustic elements of subset 32.

As shown, treatment energy is applied by independent energy source 40 as described hereinabove with reference to FIG. 1. As appropriate, energy source 40 may be mechanically independent of cuff 60, or mechanically coupled to the cuff (configuration not shown).

Typically, subset 30 is spaced apart from subset 32 at a distance L. Each subset 30 and 32 is typically but not necessarily connected to an electromechanical device 70 via lead 28. Typically, electromechanical device 70 enables monitoring of different locations of the limb. Electromechanical device 70 varies distance L between subsets 30 and 32 by moving portions of the subsets to different locations on cuff 60. Distance L is recorded by a linear encoder or other device known in the art, in order to calculate and monitor the speed of sound as described hereinabove.

Alternatively or additionally, electromechanical device 70 moves both subsets clock-wise or counter-clockwise with respect to cuff 60, maintaining distance L constant. For some applications, subsets 30 and 32 are disposed at fixed locations upon cuff 60 and electromechanical device 70 rotates cuff 60 around the limb in order to position the subsets at different locations with respect to the limb.

For some applications, during the detecting of the concentration of fat in the limb, the acoustic elements of subsets 30 and 32 are moved such that two images of the limb are obtained. The first image is reconstructed from the reflected echoes depicting a standard B-scan image, and the other image is reconstructed from the through-transmitted waves, using ultrasonic tomography algorithms known in the art. The second image may depict a map of SOS and/or mu in the imaged region.

For some applications, system 20 scans the limb and provides maps of tissue 24 before and after the treatment. In an embodiment, the treatment procedure is applied by a robotic system to the entire limb.

Figure 4A:
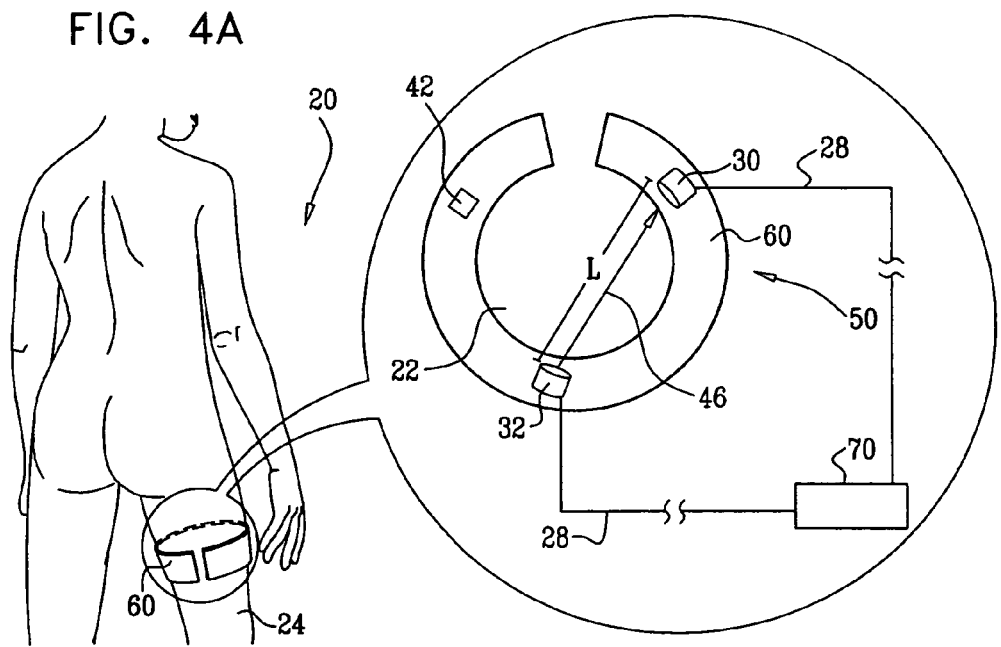
FIGS. 4A and 4B are schematic illustrations of the monitoring device of FIG. 3 comprising the treatment device, in accordance with respective embodiments of the present invention.
Figure 4B:
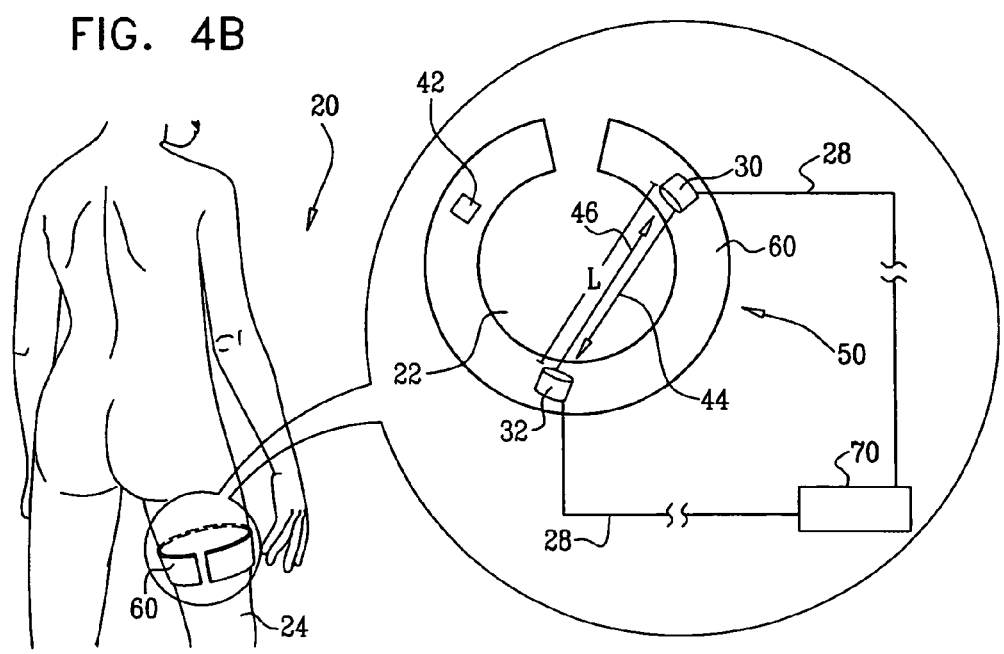

Reference is now made to FIGS. 4A and 4B, which are schematic illustrations of system 20 similar to the embodiments described hereinabove with reference to FIGS. 2A and 2B, respectively, with the exception that housing 50 comprises cuff 60. In FIG. 4A, treatment energy is transmitted only from subset 32 to subset 30 (as indicated by arrow 46), and in FIG. 4B, treatment energy is transmitted in both directions (as indicated by arrows 44 and 46).

Figure 5:
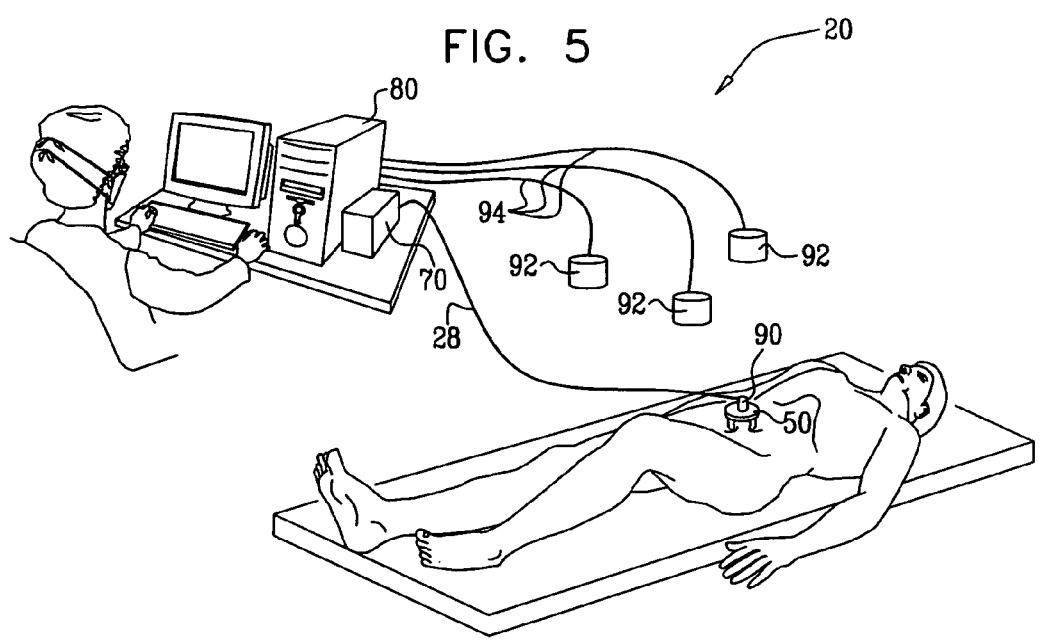
FIGS. 5 and 6 are schematic illustrations of a tracking system associated with the devices of FIGS. 1-4B, in accordance with an embodiment of the present invention.
Figure 6:
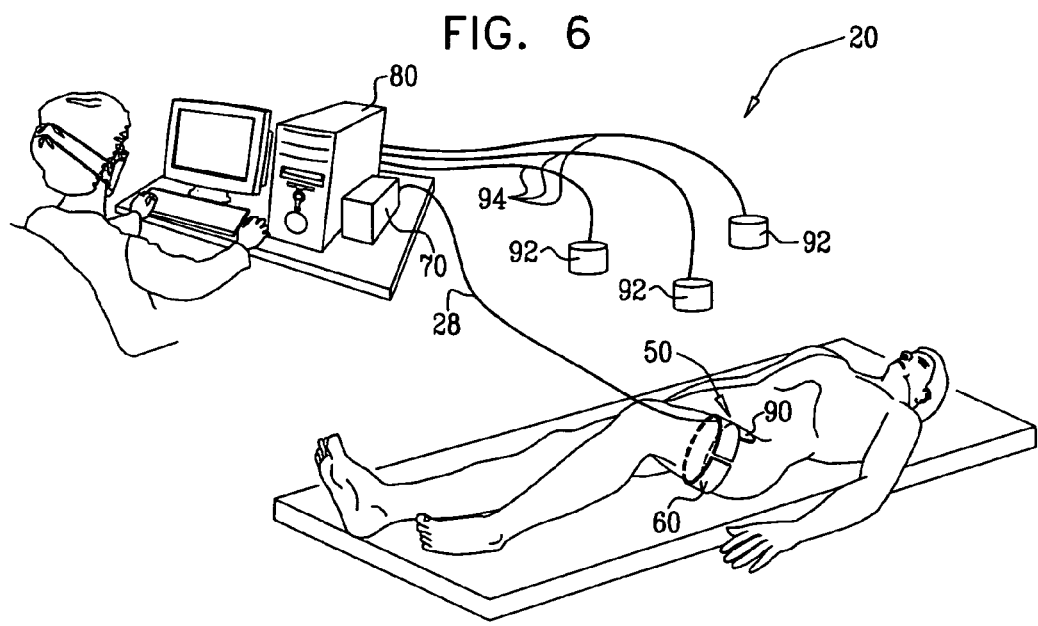

FIGS. 5 and 6 show system 20 comprising a tracking system comprising a plurality of reference sensors 92, in accordance with an embodiment of the present invention. Reference sensors 92 can be implemented in combination with each of the described embodiments of FIGS. 1-4B, and assess the location of treated tissue 24 by registering the relative spatial coordinates of the acoustic elements and/or anatomy of the patient. The sensed information is transmitted to a processing unit 80 by leads 94 coupled to reference sensors 92. Storing the location of treated areas allows for improved follow-up and comparison of treatments conducted on different days. For some applications, location sensing is performed in conjunction with the treatment to help ensure that (1) treatment has been applied to all subsections of a designated area, and/or (2) treatment has not been applied multiple times to the same subsection during a single session. Thus, for some applications, treatment locations during one session are stored, to facilitate treatments in subsequent locations being initiated outside of already-treated regions.

Typically, housing 50 comprises a sensor 90 in communication with reference sensors 92. For some applications, reference sensors 92 are placed at predetermined locations in the treatment room. Spatial localization of housing 50 with respect to coordinates of the room is achieved when reference sensors 92 transmit signals to sensor 90 (or vice versa, or when a spatial relationship is determined between sensors 92 and sensor 90). The localization can be based on measurements using electromagnetic waves (e.g., RF-induced currents in mutually-perpendicular coils), optical information (e.g., by processing video acquired by each of sensors 92) or acoustic waves (e.g., by time-of-flight measurements). In an embodiment, sensor 90 receives signals and transmits signals back to reference sensors 92 (or vice versa). The signals are subsequently transmitted to processing unit 80. For some applications, the signals transmitted from reference sensors 92 form an electromagnetic field around the patient, capable of being sensed by sensor 90. In such an embodiment, sensor 90 communicates either actively or passively with reference sensors 92, (e.g., passive communication may utilize radio frequency identification techniques known in the art).

For some applications, reference sensors 92 are placed at predetermined locations on the body of the subject (e.g., sternum, patella, pelvis, navel, etc.), and spatial localization of the housing and treated tissue relative to the anatomical landmarks is achieved.

In some embodiments, the spatial localization procedure is initiated by an operator, e.g., using a wand comprising reference sensor 92. The operator contacts predetermined anatomical landmarks of the patient and references the coordinates thereof with respect to housing 50.

For some applications, the spatial location of housing 50 during the treatment procedure is automatically registered along with other details such as intensity and duration of each treatment stage. This information is stored in processing unit 80 and used in following sessions as a reference for monitoring the treatment process.

For some applications, techniques described herein are practiced in combination with techniques described in one or more of the references cited in the Cross-references section or Background section of the present patent application, which are incorporated herein by reference.

Embodiments of the present invention described herein may be used, for example, for cosmetic purposes, such as by placing subsets 30 and 32 in contact with skin of the patient and treating fatty tissue. The scope of the present invention includes application of the techniques described herein to non-cosmetic skin treatments and to tissue other than skin, as well. For example, acoustic elements may be sized for placement during surgery on an intrabody organ of the subject, such as the heart or an abdominal organ.

It is noted that although some embodiments of the present invention are described with respect to the use of ultrasound, the scope of the present invention includes replacing the ultrasound transducers described herein with transducers of other forms of energy, such as electromagnetic radiation.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
   a housing adapted for placement on tissue that includes skin of a subject, the housing comprising first and second pinching elements configured to pinch a portion of the skin therebetween;
   a plurality of acoustic elements disposed at respective locations with respect to the housing, comprising at least a first and a second subset of the acoustic elements, coupled respectively to the first and second pinching elements, wherein the first subset is configured to transmit energy through the pinched skin, such that at least a portion of the transmitted energy reaches the second subset by through transmission through the skin; and
   a distance sensor, configured to sense a distance between the first and second subsets of the acoustic elements,
   wherein the apparatus is configured to:
      use at least some of the plurality of acoustic elements to monitor the tissue in response to the through-transmitted energy, by measuring a time-of-flight of the through-transmitted energy and calculating an indication of speed of sound in the tissue, based on a relationship between (a) the measured time-of-flight of the through-transmitted energy and (b) the distance sensed between the first and second subsets by the distance sensor, the relationship being that the speed of sound in the tissue is a division of (i) the distance sensed between the first and second subsets, by (ii) the measured time-of-flight of the through-transmitted energy,
      based on the calculated indication of the speed of sound, assess whether a concentration of fat in the tissue is sufficient for application of treatment energy thereto, and
      use at least some of the plurality of acoustic elements to apply treatment energy, and, once treatment energy has been applied to the tissue: (a) monitor temperature of the tissue by monitoring changes in the calculated indication of the speed of sound, in response to the application of the treatment energy, and (b) regulate the application of the treatment energy to the tissue, based on the monitoring of the temperature.

2. The apparatus according to claim 1, wherein the housing is flexible at least in part, and configured to flex to match the shape of the tissue.

3. The apparatus according to claim 1, comprising a source of suction configured to draw the tissue into the housing, wherein the plurality of acoustic elements are disposed with respect to the housing so as to direct the energy to the tissue within the housing.

4. The apparatus according to claim 1, wherein the first subset is configured to substantially avoid transmitting energy out of a plane defined by the housing.

5. The apparatus according to claim 1, wherein the first subset comprises ultrasound transducers.

6. The apparatus according to claim 1, wherein the first subset is configured to transmit at least some of the treatment energy.

7. The apparatus according to claim 6, wherein the first subset is configured to configure the at least some of the treatment energy for lipolysis of adipose tissue.

8. The apparatus according to claim 1, wherein the apparatus comprises an electromechanical device configured to move at least a portion of the plurality of acoustic elements.

9. The apparatus according to claim 1, comprising an energy source that is not an acoustic element from the first or second subsets of acoustic elements, and wherein the energy source is configured to transmit treatment energy in response to the monitoring.

10. The apparatus according to claim 9, wherein the energy source is configured to configure the treatment energy for lipolysis of adipose tissue.

11. The apparatus according to claim 9, wherein the energy source is configured to transmit treatment energy in conjunction with the monitoring.

12. The apparatus according to claim 1, wherein the plurality of acoustic elements is configured to effect contouring of the body of the subject.

13. The apparatus according to claim 12, comprising a sensor coupled to the housing, configured to identify a location of the housing.

14. The apparatus according to claim 12, comprising a sensor coupled to the housing, configured to identify a location of tissue, and a processing unit, configured to compare the location with a previously-stored location of tissue.

15. Apparatus, comprising:
a cuff housing configured to surround a portion of a limb that includes skin of a subject;
a plurality of acoustic elements coupled to the cuff housing at respective locations around the cuff housing, comprising at least a first and a second subset of the acoustic elements, wherein the first subset is configured to transmit energy through the skin such that at least a portion of the transmitted energy reaches the second subset by through transmission through the skin; and,
a distance sensor, configured to sense a distance between the first and second subsets of the acoustic elements,
wherein the apparatus is configured to:
use at least some of the plurality of acoustic elements to monitor the limb in response to the through-transmitted energy, by measuring a time-of-flight of the through-transmitted energy and calculating an indication of speed of sound in the limb, based on a relationship between (a) the measured time-of-flight of the through-transmitted energy and (b) the distance sensed between the first and second subsets by the distance sensor, the relationship being that the speed of sound in the tissue is a division of (i) the distance sensed between the first and second subsets, by (ii) the measured time-of-flight of the through-transmitted energy,
based on the calculated indication of the speed of sound, assess whether a concentration of fat in the limb is sufficient for application of treatment energy thereto, and
use at least some of the plurality of acoustic elements to apply treatment energy and, once treatment energy has been applied to the limb: (a) monitor temperature of the limb by monitoring changes in the calculated indication of the speed of sound, in response to the application of the treatment energy, and (b) regulate the application of the treatment energy to the limb, based on the monitoring of the temperature.

16. Apparatus, comprising:
a housing adapted for placement on tissue that includes skin of a subject;
a plurality of acoustic elements coupled to respective locations with respect to the housing, comprising at least a first and a second subset of the acoustic elements, wherein the first subset is configured to transmit energy through the skin in a plane defined by the housing, such that at least a portion of the transmitted energy reaches the second subset by through-transmission through the skin; and
a distance sensor, configured to sense a distance between the first and second subsets of the acoustic elements,
wherein the apparatus is configured to:
use a portion of the plurality of acoustic elements to facilitate monitoring of the tissue in response to the through-transmitted energy, by measuring a time-of-flight of the through-transmitted energy and calculating an indication of speed of sound in the tissue, based on a relationship between (a) the measured time-of-flight of the through-transmitted energy and (b) the distance sensed between the first and second subsets by the distance sensor, the relationship being that the speed of sound in the tissue is a division of (i) the distance sensed between the first and second subsets, by (ii) the measured time-of-flight of the through-transmitted energy,
based on the calculated indication of the speed of sound, assess whether a concentration of fat in the tissue is sufficient for application of treatment energy thereto, and
apply treatment energy and, once treatment energy has been applied to the tissue, (a) monitor temperature of the tissue by monitoring changes in the calculated indication of the speed of sound, in response to the application of the treatment energy, and (b) regulate the application of the treatment energy to the tissue, based on the monitoring of the temperature.

17. A method comprising:
providing apparatus, the apparatus including (a) a housing adapted for placement on tissue that includes skin of a subject, the housing including first and second pinching elements configured to pinch a portion of the skin therebetween; (b) a plurality of acoustic elements disposed at respective locations with respect to the housing, including at least a first and a second subset of the acoustic elements, coupled respectively to the first and second pinching elements, wherein the first subset is configured to transmit energy through the pinched skin, such that at least a portion of the transmitted energy reaches the second subset by through transmission through the skin; and (c) a distance sensor, configured to sense a distance between the first and second subsets of the acoustic elements;
using at least some of the plurality of acoustic elements to monitor the tissue in response to the through-transmitted energy, by measuring a time-of-flight of the through-transmitted energy and (b) the distance sensed between the first and second subsets by the distance sensor, the relationship being that the speed of sound in the tissue is a division of (i) the distance sensed between the first and second subsets, by (ii) the measured time-of-flight of the through-transmitted energy;
assessing, based on the calculated indication of the speed of sound, whether a concentration of fat in the tissue is sufficient for application of treatment energy thereto;
using at least some of the plurality of acoustic elements to apply treatment energy; and
once treatment energy has been applied to the tissue, (a) monitoring temperature of the tissue by monitoring changes in the calculated of the speed of sound, in response to the application of the treatment energy, and (b) regulating the application of the treatment energy to the tissue, based on the monitoring of the temperature.

18. A method comprising:
providing apparatus, the apparatus including: (a) a cuff housing configured to surround a portion of a limb that includes skin of a subject; and (b) a plurality of acoustic elements coupled to the cuff housing at respective locations around the cuff housing, the plurality of acoustic elements including at least a first and second subset of the acoustic elements, wherein the first subset is configured to transmit energy through the skin such that at least a portion of the transmitted energy reaches the second subset by the transmission through the skin; and (c) a distance sensor, configured to sense a distance between the first and second subsets of the acoustic elements;
using at least some of the plurality of acoustic elements to monitor the limb in response to the trough-transmitted energy, by measuring a time-of-flight of the trough-transmitted energy and calculating an indication of speed of sound in the limb, based on a relationship between (a) the measured time-of-flight of the through-transmitted energy and (b) the distance sensed between the first and second subsets by the distance sensor, the relationship being that the speed of sound in the tissue is a division of (i) the distance sensed between the first and second subsets, by (ii) the measured time-of-flight of the through-transmitted energy;
assessing, based on the calculated indication of the speed of sound, whether a concentration of fat in the limb is sufficient for application of treatment energy thereto;
using at least some of the plurality of acoustic elements to apply treatment energy; and
once treatment energy has been applied to the limb: (a) monitoring temperature of the limb by monitoring changes in the calculated indication of the speed of sound, in response to the application of the treatment energy, and (b) regulating the application of the temperature.

19. A method comprising:
providing apparatus, the apparatus including: (a) a housing adapted for placement on tissue that includes skin of a subject; (b) a plurality of acoustic elements coupled to respective locations with respect to the housing, including at least a first and a second subset of the acoustic elements, wherein the first subset is configured to transmit energy through the skin in a plane defined by the housing, such that at least a portion of the transmitted energy reaches the second subset by through-transmission through the skin; and (c) a distance sensor, configured to sense a distance between the first and second subsets of the acoustic elements;
using a portion of the plurality of acoustic elements to facilitate monitoring of the tissue in response to the through-transmitted energy, by measuring a time-of-flight of the through-transmitted energy and calculating an indication of speed of sound in the tissue, based on a relationship between (a) the measured time-of-flight of the through-transmitted energy and (b) the distance sensed between the first and second subsets by the distance sensor, the relationship being that the speed of sound in the tissue is a division of (i) the distance sensed between the first and second subsets, by (ii) the measured time-of-flight of the through-transmitted energy,
assessing, based on the calculated indication of the speed of sound, whether a concentration of fat in the tissue is sufficient for application of treatment energy thereto,
applying treatment energy; and
once treatment energy has been applied to the tissue, (a) monitoring temperature of the tissue by monitoring changes in the calculated indication of the speed of sound, in response to the application of the treatment energy, and (b) regulating the application of the treatment energy to the tissue, based on the monitoring of the temperature.

\* \* \* \* \*